United States Patent [19]

Onofrj

[11] Patent Number: 4,663,352

[45] Date of Patent: May 5, 1987

[54] USE OF SOME ALKANOYL L-CARNITINES FOR THE THERAPEUTICAL TREATMENT OF IDIOPATHIC AND INDUCED PARKINSONISM

[75] Inventor: Marco Onofrj, Pescara, Italy

[73] Assignee: Sigma-Tau Industrie Farmaceutiche Riunite S.p.A., Rome, Italy

[21] Appl. No.: 869,083

[22] Filed: May 30, 1986

[30] Foreign Application Priority Data

Jun. 11, 1985 [IT] Italy ............................ 48206 A/85

[51] Int. Cl.⁴ ........................................... A61K 31/205
[52] U.S. Cl. ................................................... 514/556
[58] Field of Search ............................. 514/546, 556

[56] References Cited

U.S. PATENT DOCUMENTS 4,343,816  8/1962  Cavazza ............................ 514/556
4,464,393  8/1984  Cavazza ............................ 514/556
4,537,772  8/1985  Alexander et al. ................ 514/556

Primary Examiner—Stanley J. Friedman
Attorney, Agent, or Firm—Bruce M. Collins

[57] ABSTRACT

A novel therapeutical use of some alkanoyl L-carnitines, e.g. acetyl L-carnitine, is disclosed which, orally or parenterally administered, are effective in the treatment of symptoms of idiopathic Parkinson's disease.

3 Claims, No Drawings

USE OF SOME ALKANOYL L-CARNITINES FOR THE THERAPEUTICAL TREATMENT OF IDIOPATHIC AND INDUCED PARKINSONISM

The present invention relates to a novel therapeutical utilization of some alkanoyl L-carnitines. More specifically, it relates to the use of alkanoyl L-carnitines having general formula

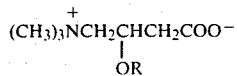

wherein R is selected from acetyl, propionyl, butyryl, hydroxybutyryl, valyl and isoleucyl, and their pharmacologically acceptable salts, for the therapeutical treatment of idiopathic Parkinson's disease and a syndrome similar to idiopathic parkinsonism induced by either self-administration of some illicit drug preparations or organism's exposure to an environment polluted by these drugs.

This invention also relates to orally or parenterally administrable pharmaceutical compositions comprising the above-identified alkanoyl L-carnitines as active principles for the treatment of the previously mentioned pathologies. In the description which follows, reference will be made, for the sake of simplicity, to acetyl L-carnitine, it being, however, understood that the disclosures concerning this specific compound equally apply to the other mentioned alkanoyl derivatives of carnitine.

Previous therapeutical uses of acetyl L-carnitine and other alkanoyl derivatives of carnitine are already known. For instance, the U.S. Pat. No. 4,194,006 discloses the use of acetyl carnitine in the therapeutical treatment of myocardial arrythmias and ischemias. The U.S. Pat. No. 4,343,816 discloses the use of acetyl carnitine in the therapeutical treatment of functional peripheral vascular diseases of arteries, such as Reynaud's disease and acrocyanosis.

The U.S. Pat. No. 4,346,107 discloses the therapeutical effectiveness of acetyl carnitine in the treatment of patients suffering from impaired cerebral metabolism as it occurs in senile and pre-senile dementia.

There is no relationship at all, however, between the already known therapeutical utilizations of the previously mentioned alkanoyl L-carnitines and the novel utilization which is the subject matter of the present invention.

This will appear more evident from the description which follows when reference is made to some recent studies which lead one to hypothesize a toxic cause of Parkinson's disease.

It is well known that, although Parkinson's disease is generally regarded as an idiopathic condition, parkinsonism symptoms may develop as a result of certain drug overdose, such as phenothiazines, butyrophenones and reserpine. Recently, Parkinsonism has been studied in drug addicts who had self-injected meperidine-like compounds whose illicit synthesis had produced MPTP and MPPP as side-products.

In fact, 1-methyl-4-phenyl-1,2,3,6-tetrahydropyridine (MPTP or NMPTP) and 1-methyl-4-phenyl-4-propoxypiperidine (MPPP) selectively destroy dopaminergic neurons in the substantia nigra and produce a Parkinson-like syndrome in man and in non-human primates which is similar to idiopathic Parkinson's disease in its clinical, pathological, biochemical and pharmacological response features. (Davis et al., Chronic Parkinsonism secondary to intravenous injection of meperidine analogues, Phychiatry Res 1, 249–254 (1979); Langston et al., Chronic Parkinsonism in humans due to a product of meperidine-analog synthesis, Science 219,979–980 (1983); Burns et al., A primate model of parkinsonism: Selective destruction of dopaminergic neurons in the pars compacta of the substantia nigra by N-methyl-4-phenyl-1,2,3,6-tetrahydropyridine, Proc. Natl. Acad. Sci. USA, 80,4546–4550, July 1983). The degree of similarity between idiopathic Parkinson's disease and MPTP-induced parkinsonism is so high that recently it has been hypothesized (Burns et al., The neurotoxicity of 1-methyl-4-phenyl-1,2,3,6-tetrahydropyridine in the monkey and man, Can. J. Neur.Sci. 11, n.1 (supplement), 166–168, February 1984) that MPTP-induced parkinsonism "may represent more than a model. The occurrence of MPTP-induced parkinsonism leads one to consider a toxic cause for Parkinson's disease".

The present therapy of choice for the treatment of parkinsonism is the administration of Levodopa (L-dopa), the metabolic precursor of dopamine which itself does not cross the blood-brain barrier. Levodopa must be administered in large doses because most of the drug is metabolized before it reaches its sites of action in the brain. L-dopa is, therefore, administered in combination with carbidopa, a dopa decarboxylase inhibitor which prevents the systemic metabolism of levodopa before it reaches the brain. If levodopa is administered alone, side-effects are experienced, such as anorexia, nausea and vomiting, and orthostatic hypotension which remarkably subside, however, as soon as also carbidopa is administered. After a few months of L-dopa therapy, even though it is administered in combination with the decarboxylase inhibitor, further bothersome side effects, such as dyskinesias of the face, trunk and limbs, may be experienced.

The onset of these dyskinesias evidences, at best, that the drug dose has reached a critical threshold which should not be exceeded. However, L-dopa's most serious drawback is that its early effectiveness subsides with time: a progressive worsening of symptomatology ensues after 3 to 7 years of continuous therapy.

Moreover, as the parkinsonism syndrome slowly worsens with time, the onset of fast clinical changes (so called "on-off" conditions) is frequently noticed: an almost normal mobility ("on" conditions) for 1-2 hours following L-dopa administration reverses to a substantially complete akinesia ("off" condition). These "on-off" conditions are never detected before the beginning of L-dopa therapy.

This progressive loss of effectiveness and the onset of "on-off" conditions raise the problem of the "after-dopa" therapy: early treatment of the disease with anti-cholinergic agents only; administration of the minimum effective dose of L-dopa; use of L-dopa in combination with bromocriptine and ergoline derivatives, such as lergotrile, pergolide and lisuride. However, also these pharmaceuticals present bothersome drawbacks. For instance, bromocriptine side effects are similar to those of L-dopa. In some cases, these side effects, (emotional disturbances, vertigos, erythromelalgia) are so relevant that the treatment must be interrupted. It has been now found that the use of an alkanoyl L-carnitine of general formula

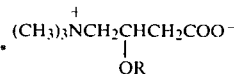

wherein R is selected from acetyl, propionyl, butyryl, hydroxybutyryl, valyl and isoleucyl is effective for the therapeutical treatment of symptoms of idiopathic Parkinson's disease.

The foregoing alkanoyl L-carnitines do not present the abovementioned drawbacks, toxic and side-effects of L-dopa and the other pharmaceuticals currently used for the treatment of parkinsonism. The effectiveness of the foregoing alkanoyl L-carnitine is surprising insofar as there is no structural relationship between them and L-dopa or the other mentioned pharmaceuticals. The effect of Parkinson-like symptoms can be conveniently observed in laboratory models.

Thus, a Parkinson-like syndrome was induced in the experiment animals following the procedure disclosed by Cohen et al., in European Journal of Pharmacology 106,209–210 (1984).

35 Cynomolgus monkeys (Macaca fascicularis), weighing 2.1–2.8 kg were used in this study. Eight monkeys were used as controls. 18 monkeys (MPTP-monkeys) were administered 0.35 mg/kg i.v. once a day of 1-methyl-4-phenyl-1,2,3,6-tetrahydropyridine (MPTP, free) base) for 4 consecutive days. All the 18 animals developed parkinsonism, the typical symptoms appearing 2 to 4 days after administration. The symptoms were: anorexia (after 2 days), bradykinesia, tremor (after 3–4 days), freezing and lack of facial expression (after 3–5 days). 9 days after MPTP administration the animals showed sharp alterations in the acoustical, visual and somatosensory bioelectrical evoked responses. It was found that MPTP had reduced the amplitude of these responses by 70%. The response latency increased by 25–60 msec. One monkey (acetyl L-carnitine prior MPTP monkey), which was then treated with MPTP as previously described, was administered a single dose of acetyl L-carnitine (5 mg/kg i.m.) 3 days before the first MPTP administration. This animal develop the first symptom (i.e. anorexia) after 11 days. Bradykinesia, freezing, tremor and lack of facial expression developed only after 13 days.

Other six monkeys (MPTP+acetyl L-carnitine monkeys) which were then treated with MPTP as previously described, were administered acetyl L-carnitine (5 mg/kg i.m.) for 3 days before the first MPTP dose was administered.

5 mg/kg i.m. of acetyl L-carnitine were administered on the same days of the MPTP treatment. During the 5 days following the end of MPTP treatment, the animals were administered daily doses of acetyl L-carnitine (5 mg/kg i.m.). 60 days following the end of treatment with acetyl L-carnitine, no animal had developed any Parkinsonism's symptom. All these monkeys showed normal evoked responses.

In two monkeys (MPTP delayed acetyl L-carnitine monkeys) MPTP was administered for 3 days as previously described. Acetyl L-carnitine (20 mg/kg) were then injected i.m. for 20 days beginning on the 3rd day after the last MPTP administration. In these monkeys, decrement of food intake and bradykinesia appeared as early as in the monkeys which had been administered MPTP only.

However, a steady reduction of symptoms was noticed already on the 21th day following the last MPTP injection.

The "MPTP"-monkeys were sacrificed 90–180 days following the last injection. The "acetyl L-carnitine prior MPTP" monkey was sacrificed 30 days following the last MPTP injection. The "MPTP delayed acetyl L-carnitine" monkeys were sacrificed 60 days following the last MPTP injection. The "MPTP+acetyl L-carnitine" monkeys were sacrificed 60–350 days following the last injection. On the day of sacrifice the animals were killed by sodium pentobarbital, the brains and eyes were excised and frozen at $-20°$ C.

Biochemical and neuropathological studies performed in the sacrificed animals showed a decrement of dopamine and homovanilic acid in the caudate, striatum and neuronal loss of as much as 90% in "MPTP" monkey and in the "ALC prior MPTP" monkey (ALC=acetyl L-carnitine).

The same measurements were inside normal limits in "MPTP+ALC" monkeys. In the "MPTP delayed ALC" monkeys post mortem measurements showed a 40% decrement of dopamine in the striatum and 30% neuronal loss in the nigra.

Further studies have ascertained that, although the daily dose to be administered depends on the age, weight and general condition of the subject, utilizing sound professional judgement, generally, from about 1 to about 30 mg of acetyl L-carnitine/kg of body weight/day is a suitable dose.

Acetyl L-carnitine is compounded into the pharmaceutical compositions by using the usual excipients which are well-known in pharmaceutical technology for preparing orally and parenterally administrable compositions.

It has also been found that a pharmaceutical composition in unit dosage form which is particularly suited for the foregoing therapeutical utilization comprises from about 50 to about 1,000 mg of acetyl L-carnitine.

Some non-limiting examples of pharmaceutical compositions suitable for oral and parenteral administration are illustrated herebelow:

| TABLETS | | |
|---|---|---|
| Acetyl L-carnitine HCl | mg | 586 |
| | (corresponding to 500 mg of inner salt) | |
| Polyvinylpyrrolidone | mg | 60 |
| AVICEL PH 101 | mg | 17 |
| Magnesium Stearate | mg | 20 |
| Cellulose acetophtalate | mg | 18 |
| Ethyl phtalate | mg | 7,5 |
| Silicone oil AK 100 | mg | 3 |
| CAPSULES | | |
| Acetyl L-carnitine | mg | 586 |
| | (corresponding to 500 mg of inner salt) | |
| AEROSIL 200 | mg | 6 |
| Magnesium Stearate | mg | 25 |
| 5 gram SACHETS | | |
| Acetyl L-carnitine | mg | 1,172 |
| | (corresponding to 1,000 mg of inner salt) | |
| Sodium citrate | mg | 300 |
| METHOCEL E 5 | mg | 100 |
| Levulose | mg | 1,500 |
| AEROSIL 200 | mg | 25 |
| Saccarose, balance to | mg | 5,000 |
| 5 ml - INJECTABLE PHIALS | | |

| -continued | | |
|---|---|---|
| Lyophilized ingredients: | | |
| Acetyl L-carnitine | mg | 586 (corresponding to 500 mg of inner salt) |
| Glycocoll | mg | 750 |
| Solvent: | | |
| Water for injections | ml | 5 |

What is claimed is:

1. A method of treating parkinsonism-like symptoms in a human, which comprises orally or parenterally administering to the human in a single or multiple dose administration regimen an amount of an alkanoyl L-carnitine of formula

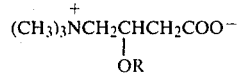

wherein R is selected from the group consisting of acetyl, propionyl, butyryl, hydroxy-butyryl, valyl and isoleucyl, or a pharmaceutically acceptable salt thereof, which is sufficient upon administration according to said regimen to achieve in said patient an anti-parkinsonism effect.

2. The method of claim 1, wherein the total amount administered per day per kg of body weight is from about 1 to about 30 mg of at least one member selected from the group consisting of the alkanoyl L-carnitines of formula

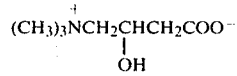

wherein R is selected from the group consisting of acetyl, propionyl, butyryl, valyl and isoleucyl, or an equivalent amount of a pharmaceutically acceptable salt thereof.

3. A method of preventing the onset in a human addicted to drugs of a chemically induced syndrome similar to idiopathic parkinsonism which comprises orally or parenterally administering to said human per day per kg of body weight from about 1 to about 30 mg of at least one member selected from the group consisting of the alkanoyl L-carnitines of formula

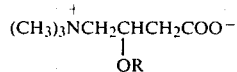

wherein R is selected from the group consisting of acetyl, propionyl, butyryl, hydroxy-butyryl, valyl and isoleucyl, or an equivalent amount of a pharmaceutically acceptable salt thereof.

* * * * *